US008940000B2

(12) United States Patent
Kasvikis et al.

(10) Patent No.: US 8,940,000 B2
(45) Date of Patent: Jan. 27, 2015

(54) SURGICAL INSTRUMENTS WITH FLEXIBLE MEMBER ATTACHMENT STRUCTURES

(75) Inventors: Dino Kasvikis, Mansfield, MA (US); Joshua Snow, Clinton, CT (US); Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 757 days.

(21) Appl. No.: 12/778,487

(22) Filed: May 12, 2010

(65) Prior Publication Data

US 2011/0282363 A1  Nov. 17, 2011

(51) Int. Cl.
| | | |
|---|---|---|
| A61B 17/10 | (2006.01) | |
| A61B 17/04 | (2006.01) | |
| A61B 17/00 | (2006.01) | |
| A61B 17/072 | (2006.01) | |
| A61B 17/12 | (2006.01) | |
| A61B 18/14 | (2006.01) | |
| A61B 18/00 | (2006.01) | |

(52) U.S. Cl.
CPC ....... *A61B 17/07207* (2013.01); *A61B 17/0483* (2013.01); *A61B 17/12009* (2013.01); *A61B 17/12013* (2013.01); *A61B 18/1445* (2013.01); *A61B 2017/07221* (2013.01); *A61B 2017/07228* (2013.01); *A61B 2018/0063* (2013.01)
USPC ............................ 606/148; 606/139; 606/205

(58) Field of Classification Search
CPC .. A61B 17/0483; A61B 17/115; A61B 17/12; A61B 17/12009; A61B 17/12013; A61B 17/0469; A61B 17/0485; A61B 2017/2945
USPC ................. 606/139, 144–147, 148, 205–207, 606/210–211; 227/175.1–182.1
See application file for complete search history.

(56) References Cited

U.S. PATENT DOCUMENTS

| | | |
|---|---|---|
| 3,017,637 A | 1/1962 | Sampson |
| 3,269,630 A | 8/1966 | Fleischer |

(Continued)

FOREIGN PATENT DOCUMENTS

| | | |
|---|---|---|
| EP | 0169044 A2 | 1/1986 |
| EP | 0 600 182 | 6/1994 |

(Continued)

OTHER PUBLICATIONS

Sayfan et al., Effect of rectal stump washout on the presence of free malignant cells in the rectum during anterior resection for rectal cancer, Diseases of the Colon and Rectum, vol. 43, Issue 12, pp. 1710-1712, Dec. 2000.*

(Continued)

*Primary Examiner* — Julian W Woo
*Assistant Examiner* — Shaun L David

(57) ABSTRACT

A surgical instrument for surgically joining tissue is disclosed. The surgical instrument includes a handle portion, an endoscopic portion, a pair of jaw members and at least one flexible member attachment structure. The endoscopic portion extends distally from the handle portion and defines a first longitudinal axis. The pair of jaw members is disposed adjacent a distal end of the endoscopic portion and extends generally distally therefrom. At least one of the jaw members is movable with respect to the other between an open position and an approximated position for engaging body tissue therebetween. The flexible member attachment structure is disposed in mechanical cooperation with at least one jaw member and is configured to facilitate the attachment of a flexible member thereto.

9 Claims, 10 Drawing Sheets

(56) References Cited

U.S. PATENT DOCUMENTS

| | | | | |
|---|---|---|---|---|
| 3,315,863 | A | 4/1967 | O'Dea | |
| 3,842,840 | A | 10/1974 | Schweizer | |
| 4,216,891 | A | 8/1980 | Behlke | |
| 4,354,628 | A | 10/1982 | Green | |
| 4,383,634 | A | 5/1983 | Green | |
| 4,506,671 | A | 3/1985 | Green | |
| 4,530,453 | A | 7/1985 | Green | |
| 4,566,620 | A | 1/1986 | Green et al. | |
| 4,568,009 | A | 2/1986 | Green | |
| 4,589,582 | A | 5/1986 | Bilotti | |
| 4,617,928 | A | 10/1986 | Alfranca | |
| 4,665,916 | A | 5/1987 | Green | |
| 4,684,051 | A | 8/1987 | Akopov et al. | |
| 4,715,520 | A | 12/1987 | Roehr, Jr. et al. | |
| 4,788,978 | A | 12/1988 | Strekopytov et al. | |
| 4,819,853 | A | 4/1989 | Green | |
| 4,869,414 | A | 9/1989 | Green et al. | |
| 4,881,544 | A | 11/1989 | Green et al. | |
| 4,881,545 | A | 11/1989 | Isaacs et al. | |
| 4,915,100 | A | 4/1990 | Green | |
| 5,100,042 | A | 3/1992 | Gravener et al. | |
| 5,318,579 | A * | 6/1994 | Chow | 606/148 |
| 5,344,060 | A | 9/1994 | Gravener et al. | |
| 5,405,073 | A | 4/1995 | Porter | |
| 5,425,737 | A * | 6/1995 | Burbank et al. | 606/144 |
| 5,452,836 | A | 9/1995 | Huitema et al. | |
| 5,465,894 | A | 11/1995 | Clark et al. | |
| 5,470,008 | A | 11/1995 | Rodak | |
| 5,547,117 | A | 8/1996 | Hamblin et al. | |
| 5,558,266 | A | 9/1996 | Green et al. | |
| 5,579,978 | A | 12/1996 | Green et al. | |
| 5,607,094 | A | 3/1997 | Clark et al. | |
| 5,706,997 | A | 1/1998 | Green et al. | |
| 5,706,998 | A | 1/1998 | Plyley et al. | |
| 5,746,757 | A * | 5/1998 | McGuire | 606/148 |
| 5,816,471 | A | 10/1998 | Plyley et al. | |
| 5,843,126 | A | 12/1998 | Jameel | |
| 6,066,160 | A | 5/2000 | Colvin et al. | |
| 6,217,592 | B1 * | 4/2001 | Freda et al. | 606/145 |
| 6,805,273 | B2 | 10/2004 | Bilotti et al. | |
| 6,988,650 | B2 | 1/2006 | Schwemberger et al. | |
| 7,147,139 | B2 | 12/2006 | Schwemberger et al. | |
| 7,204,404 | B2 | 4/2007 | Nguyen et al. | |
| 7,207,472 | B2 | 4/2007 | Wukusick et al. | |
| 2003/0065336 | A1 | 4/2003 | Xiao | |
| 2003/0233106 | A1 | 12/2003 | Dreyfuss | |
| 2004/0133238 | A1 | 7/2004 | Cerier | |
| 2005/0139636 | A1 | 6/2005 | Schwemberger et al. | |
| 2005/0145672 | A1 | 7/2005 | Schwemberger et al. | |
| 2005/0247753 | A1 | 11/2005 | Kelly et al. | |
| 2006/0163312 | A1 | 7/2006 | Viola et al. | |
| 2007/0114261 | A1 * | 5/2007 | Ortiz et al. | 227/175.1 |
| 2007/0187456 | A1 | 8/2007 | Viola et al. | |
| 2007/0250118 | A1 | 10/2007 | Masini | |
| 2007/0270885 | A1 | 11/2007 | Weinert et al. | |
| 2008/0078800 | A1 | 4/2008 | Hess et al. | |
| 2009/0012520 | A1 * | 1/2009 | Hixson et al. | 606/51 |
| 2009/0281563 | A1 | 11/2009 | Newell et al. | |
| 2009/0306684 | A1 * | 12/2009 | Stone et al. | 606/145 |
| 2010/0305581 | A1 * | 12/2010 | Hart | 606/139 |

FOREIGN PATENT DOCUMENTS

| | | |
|---|---|---|
| GB | 2029754 | 3/1980 |
| GB | 2337934 A | 12/1999 |
| WO | WO 02/30296 | 4/2002 |
| WO | WO 2006/055385 | 5/2006 |

OTHER PUBLICATIONS

European Search Report dated Jun. 28, 2011 from European Patent Application No. EP11250054.1.

European Search Report for EP 11178544 dated Sep. 29, 2011.

European Search Report EP 09251240 dated Oct. 5, 2009. (8 pages).

* cited by examiner

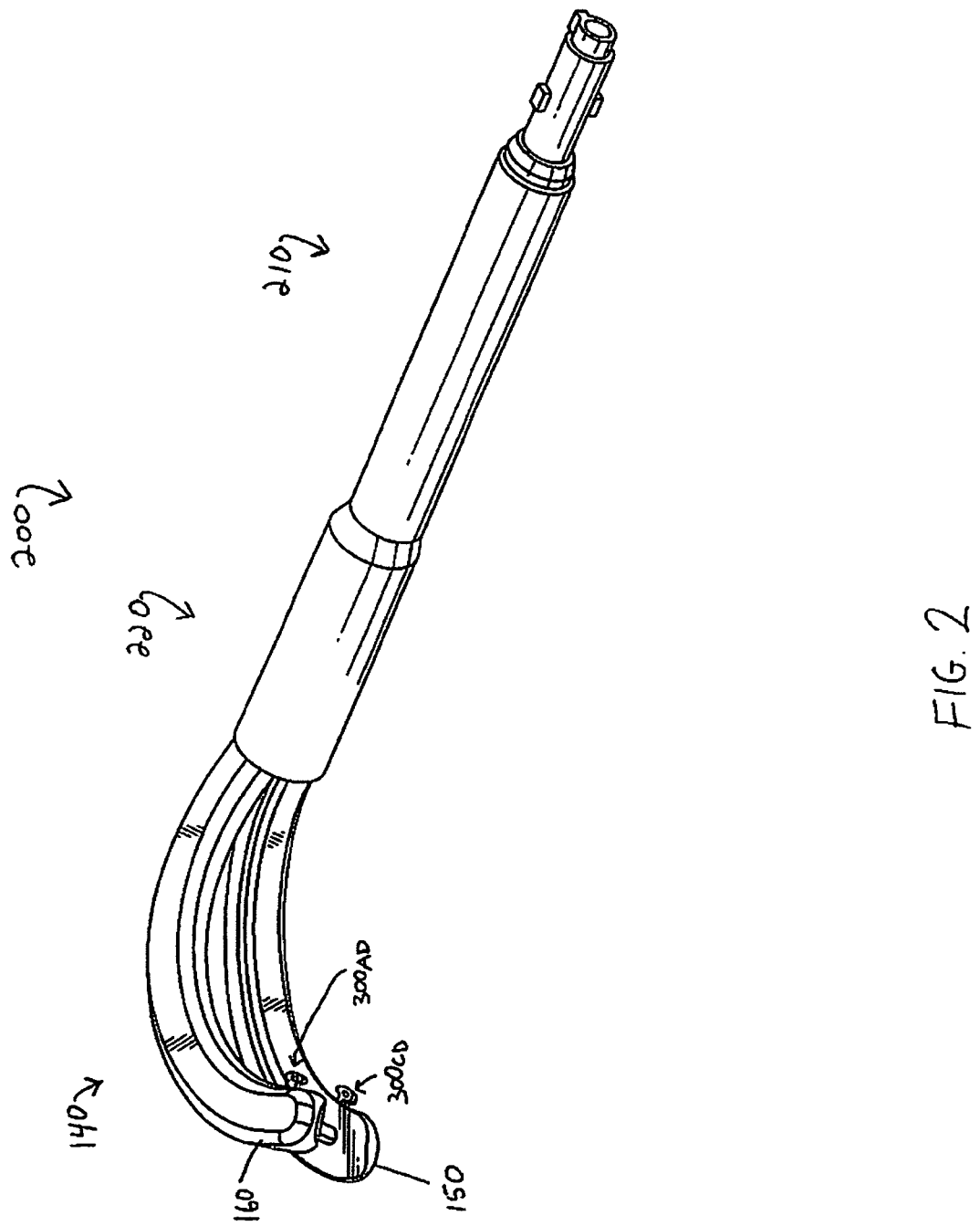

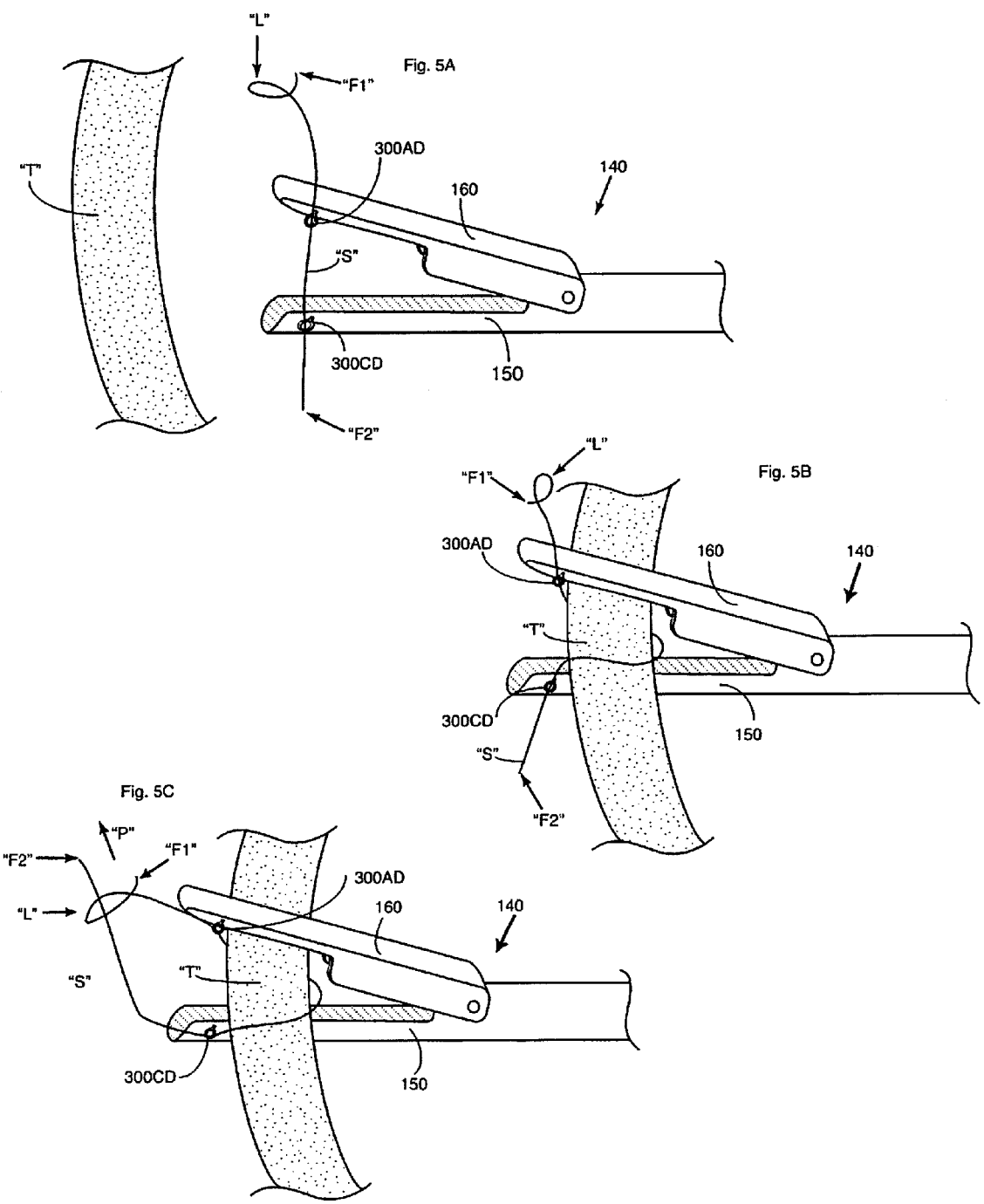

US 8,940,000 B2

SURGICAL INSTRUMENTS WITH FLEXIBLE MEMBER ATTACHMENT STRUCTURES

BACKGROUND

1. Technical field

The present disclosure relates generally to instruments for surgically joining tissue and, more specifically, to a surgical instrument including flexible member attachment structures.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

Other examples of a surgical instrument of the present disclosure include electrosurgical (e.g., monopolar and bipolar) forceps. Electrosurgical forceps utilize both mechanical clamping action and electrical energy to affect hemostasis by heating the tissue and blood vessels to coagulate, cauterize and/or seal tissue.

SUMMARY

The present disclosure relates to a surgical instrument for surgically joining tissue. The surgical instrument includes a handle portion, an endoscopic portion, a pair of jaw members and at least one flexible member attachment structure. The endoscopic portion extends distally from the handle portion and defines a first longitudinal axis. The pair of jaw members is disposed adjacent a distal end of the endoscopic portion and extends generally distally therefrom. At least one of the jaw members is movable with respect to the other between an open position and an approximated position for engaging body tissue therebetween. The flexible member attachment structure is disposed in mechanical cooperation with at least one jaw member and is configured to facilitate the attachment of a flexible member thereto.

The present disclosure also relates to a method of performing a surgical procedure. The method comprises the step of providing a surgical instrument comprising a handle portion, an endoscopic portion extending distally from the handle portion and defining a first longitudinal axis, a pair of jaw members, and at least one flexible member attachment structure. The pair of jaw members is disposed adjacent a distal end of the endoscopic portion and extends generally distally therefrom. At least one of the jaw members is movable with respect to the other between an open position and an approximated position for engaging body tissue therebetween. The at least one flexible member attachment structure is disposed in mechanical cooperation with at least one jaw member. The method also includes the steps of threading a flexible member through the flexible member attachment structure, positioning the jaw members adjacent target tissue, at least partially encircling the target tissue with at least a portion of the flexible member, and performing a surgical washout.

The present disclosure also relates to a loading unit configured for releasable engagement with a surgical instrument. The loading unit comprises a body portion, a pair of jaw members and at least one flexible member attachment structure. The body portion defines a first longitudinal axis. A proximal portion of the body portion is configured for releasable engagement with an endoscopic portion of the surgical instrument. The pair of jaw members is disposed distally of the body portion. At least one of the jaw members is movable with respect to the other between an open position and an approximated position for engaging body tissue therebetween. The flexible member attachment structure is disposed in mechanical cooperation with at least one jaw member and is configured to facilitate the attachment of a flexible member thereto.

BRIEF DESCRIPTION OF FIGURES

Various embodiments of the presently disclosed surgical instrument are disclosed herein with reference to the drawings, wherein:

FIGS. 2-3 are perspective views of a loading unit including two distally-disposed flexible member attachment structures with the jaw members open and closed, respectively, for use with the surgical instruments of FIGS. 1A-1C;

FIGS. 5A-5C are perspective views of jaw members of a surgical instrument including two distally-disposed flexible member attachment structures in accordance with embodiments of the present disclosure illustrated during the process of encircling target tissue with flexible member.

DETAILED DESCRIPTION

Figure 1A:
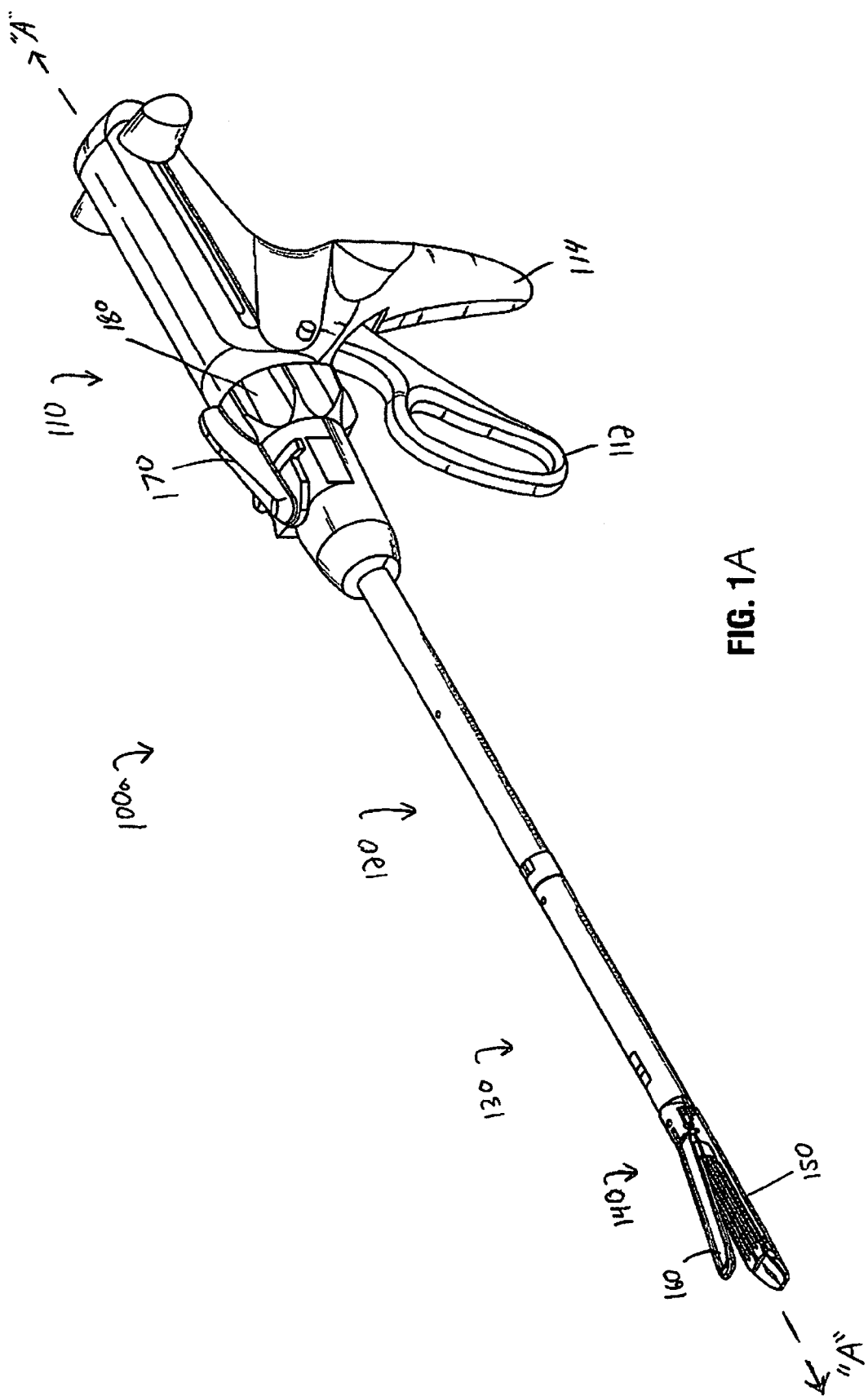
FIG. 1A is a perspective view of a surgical stapling instrument having linear jaw members in accordance with the present disclosure.

Embodiments of the presently disclosed surgical instrument, and loading unit for use therewith, are described in detail with reference to the drawings, wherein like reference numerals designate corresponding elements in each of the several views.

A surgical stapling instrument having linear jaw members of the present disclosure is indicated as reference numeral 100a in FIG. 1A. A surgical stapling instrument having curved jaw members of the present disclosure is indicated as reference numeral 100b in FIG. 1B. An electrosurgical forceps of the present disclosure is indicated as reference numeral 100c in FIG. 10. Collectively, surgical instruments 100*a*, 100*b* and 100*c* are referred to herein as reference numeral 100. Similarly, several features that are common to each surgical stapling instrument 100*a*, 100*b* and 100*c* are collectively referred to as the same reference number.

With particular reference to Figure. 1A, linear surgical stapling apparatus 100*a* includes a handle assembly 110, an endoscopic portion 120, and an end effector 130 including a pair of jaw members 140. The end effector 130 may be positioned within a body cavity to engage tissue at a surgical site while handle assembly 110 is manipulatable by a surgeon from outside the body cavity to control the movement and operation of the end effector 130. Endoscopic portion 120 defines a longitudinal axis "A-A."

Figure 3:
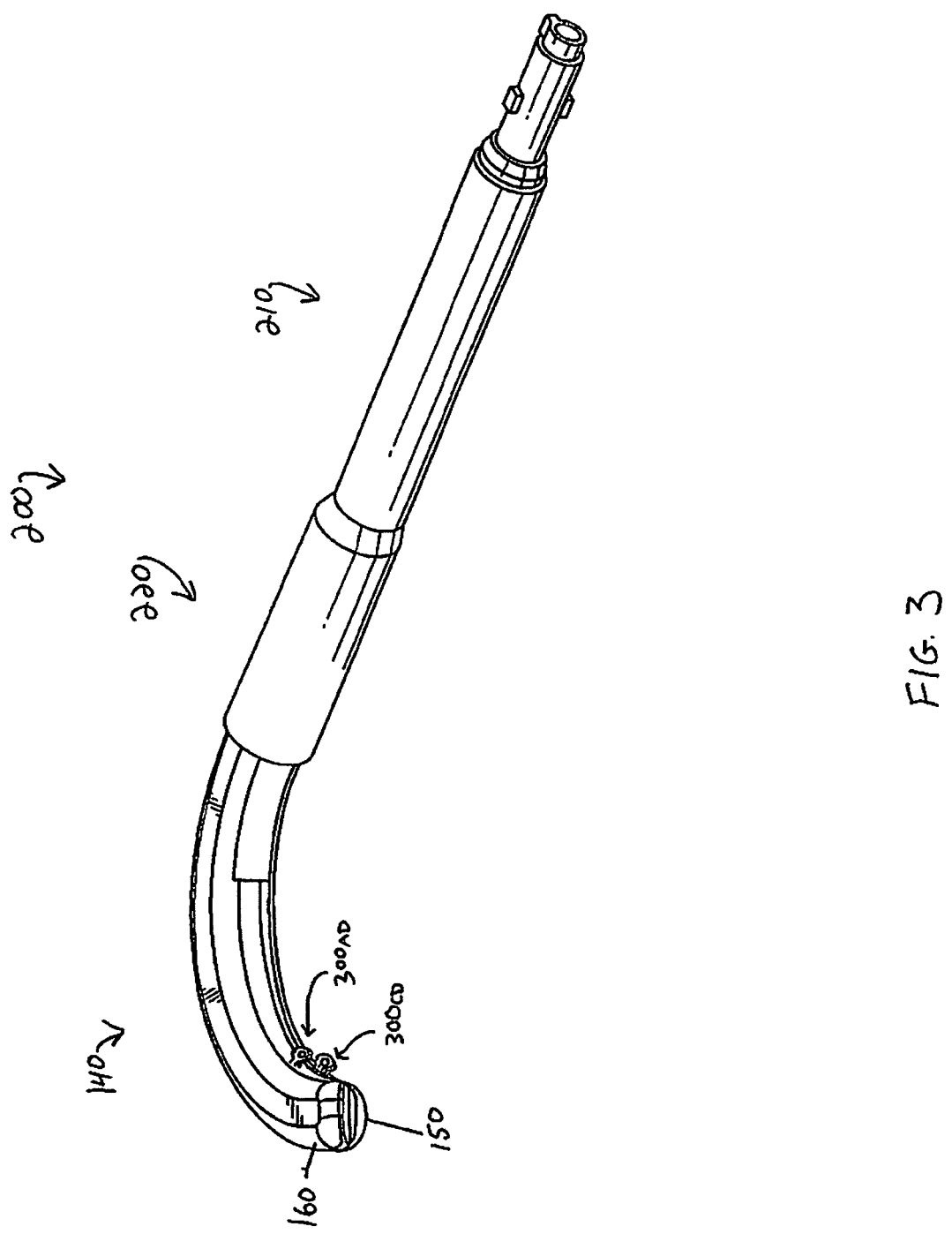

Jaw members 140 of end effector 130 include a cartridge assembly 150, which houses a plurality of staples arranged in linear rows, and an anvil assembly 160 for forming the staples. At least one of the cartridge assembly 150 and the anvil assembly 160 is movable with respect to the other between an open position (FIG. 2 shows curved jaw members in an open position) wherein the cartridge assembly 150 is substantially spaced from the anvil assembly 160 and an approximated position (FIG. 3 shows curved jaw members in an approximated position) where the cartridge assembly 150 and the anvil assembly 160 are closer together. A movable handle 112 of the handle assembly 110 is movable through an actuation stroke or strokes relative to a stationary handle 114 to move at least one of the jaw members 140 (e.g., cartridge assembly 150) in relation to the other jaw member (e.g., anvil assembly 160) between the open position and the approximated position and to eject the staples from the cartridge assembly 150 towards staple-forming pockets of the anvil assembly 160.

Further details of a linear surgical stapling instrument are described in detail in commonly-owned U.S. Pat. No. 6,953,139 to Milliman et al., the entire contents of which are hereby incorporated by reference herein.

Figure 1B:
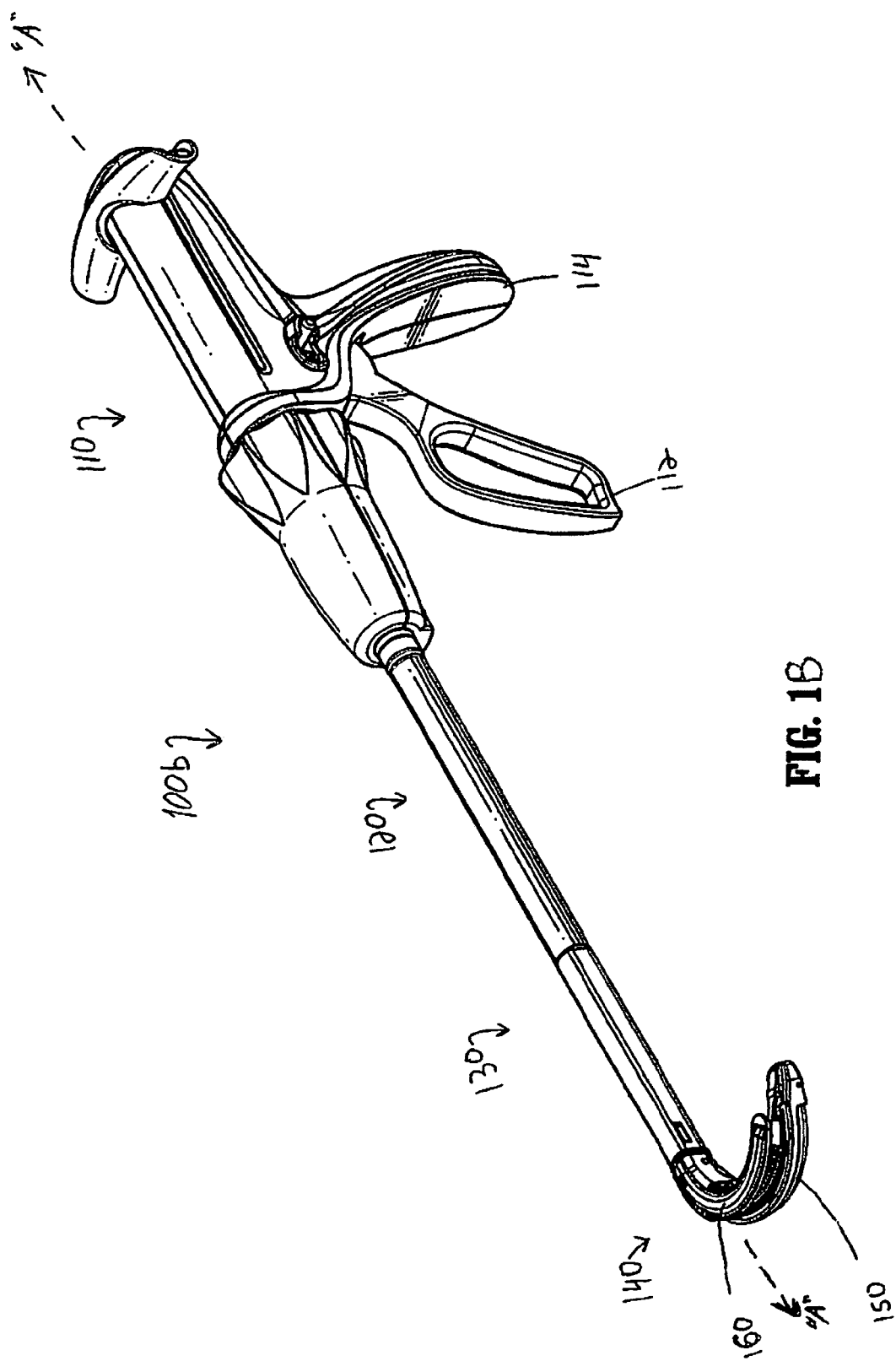
FIG. 1B is a perspective view a surgical stapling instrument having curved jaw members in accordance with the present disclosure.
Figure 1C:
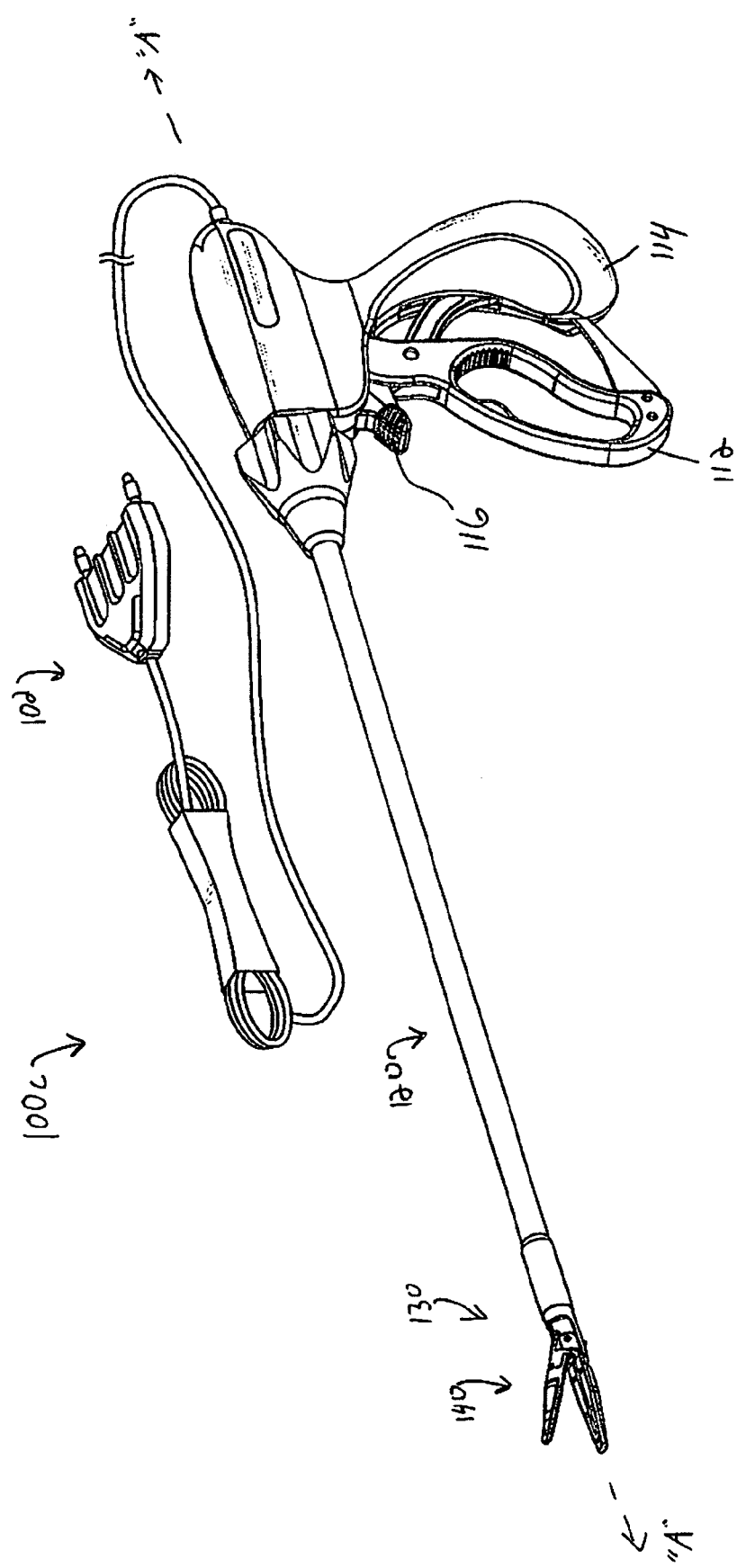
FIG. 1C is a perspective view of an electrosurgical forceps in accordance with the present disclosure.

With reference to FIG. 1B, surgical stapling apparatus 100*b* having curved jaw members 140 is shown. Surgical stapling apparatus 100*b* and linear surgical stapling apparatus 100*a* share various common features. A distinguishing feature of surgical stapling apparatus 100*b* includes its curved jaw members 140*b*. Surgical stapling apparatus 100*b* include an end effector 130 having a cartridge assembly 150 and an anvil assembly 160, that are each curved with respect to a longitudinal axis "A-A," defined by endoscopic portion 120. It is envisioned that the curved jaw members facilitate performing certain types of surgical procedures. For example, curved jaw members, as compared to linear jaw members (such as the jaw members illustrated in FIG. 1A), may help facilitate access to lower pelvic regions, e.g., during lower anterior resection ("LAR") or other colo-rectal surgery. Additionally, the inclusion of curved jaw members 140 may allow increased visualization to a surgical site and may also allow more room for a surgeon to manipulate target tissue or the jaw members 140*b* themselves with his or her hand.

In a surgical stapling instrument 100*a*, 100*b* in accordance with the present disclosure, a rod or other member is moved distally, through operation of movable handle 112, to approximate jaw members 140 and deploy the staples. For example, at least a partial actuation of movable handle 112 with respect stationary handle 114 translates a drive beam (not explicitly shown in the illustrated embodiments) longitudinally to approximate at least one jaw member with respect to the other. Additionally, at least a partial actuation (e.g., continued actuation) of movable handle 112 translates a firing rod (not explicitly shown in the illustrated embodiments) longitudinally to eject surgical fasteners (e.g., staples) from cartridge assembly 150 and/or to advance a knife to cut tissue. It is also envisioned that actuation of a first handle approximates the jaw members with respect to one another and actuation of a second handle and/or a third handle causes the ejection of fasteners and advancement of the knife. Other types of handles can be used such as, for example, motor-driven, hydraulic, ratcheting, etc.

With continued reference to FIG. 1A, a lever 170 is shown adjacent a rotation dial 180 and may be used to facilitate articulation of the jaw members 140. Actuation of lever 170 causes the jaw members 140 to move between a first position, where the jaw members 140 are substantially aligned with the longitudinal axis "A-A," and a second position, where the jaw members 140 are disposed at an angle with respect to the longitudinal axis "A-A." It is envisioned that the endoscopic portion 120 includes at least one articulation link (not explicitly shown) at least partially therein, and that a proximal portion of the articulation link is mechanically engaged with lever 170, and that a distal portion of the articulation link is mechanically engaged with at least one jaw member 140. It is further envisioned that the distal portion of the articulation link is engaged with a lateral side of one of the jaw members 140, such that, moving lever 170 which causes the articulation link to move longitudinally, results in a proximal portion of at least one jaw member moving proximally or distally. That is, moving the lever 170 in a first direction causes the articulation link to move proximally (which articulates the jaw members 140 in a first direction) and moving the lever 170 in a second, opposite direction causes the articulation link to move distally (which articulates the jaw members 140 in a second direction).

Referring now to FIG. 10, electrosurgical forceps 100*c* may also embody various aspects of the present disclosure. Electrosurgical forceps 100*c* includes a connector assembly 102 for connection to a source of electrosurgical energy (not shown). Electrosurgical forceps 100*c* includes a handle assembly 110 near a proximal end, an end effector 130 near a distal end, and an endoscopic portion 120 therebetween. The end effector 130 may be positioned within a body cavity to engage tissue at a surgical site while handle assembly 110 is manipulatable by a surgeon from outside the body cavity to control the movement and operation of the end effector 130. Handle assembly 110 includes a movable handle 112, which may be manipulated to open and close jaw members 140 of end effector 130, and a trigger 116, which may be manipulated to initiate an electrosurgical current. Further details of an electrosurgical forceps are described in U.S. Pat. No. 7,083,618, which is incorporated herein in its entirety by reference.

A single use loading unit ("SULU") or a disposable loading unit ("DLU") (collectively referred to as "loading unit 200"), which is mechanically engageable with handle portion 110 is shown in FIGS. 2-3 having curved jaw members 140. Loading unit 200 is attachable to an endoscopic portion 120 of surgical instrument 100, e.g., to allow surgical stapling instrument 100 to have greater versatility. Loading unit 200 may be configured for a single use, and/or may be configured to be used more than once. Loading unit 200 includes a proximal body portion 210 and a tool assembly 220, which includes jaw members 140. Jaw members 140 of loading unit 200 include a cartridge assembly 150, and an anvil assembly 160. Loading unit also includes an actuation mechanism for affecting movement of at least one of the cartridge assembly 150 and the anvil assembly 160 relative to the other, and for ejecting fasteners from the cartridge assembly 150. Proximal body portion 210 is configured to removably attach to endoscopic portion 120 of surgical instrument 100 using a variety of attachment features, such as, for example, a bayonet coupling, latch, detent or snap-fit. Examples of loading units for use with a surgical instrument are disclosed in commonly-owned U.S. Pat. No. 5,752,644 to Bolanos et al., the entire contents of which are hereby incorporated by reference herein.

Figure 3A:
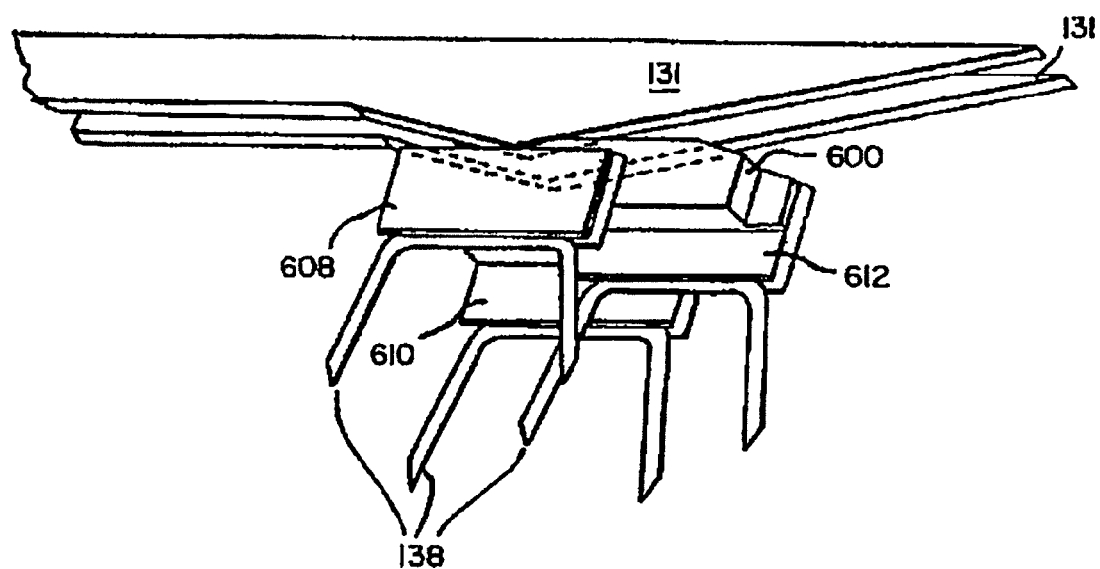
FIG. 3A is a perspective view of a loading unit including cam bar and pushers in accordance with an embodiment of the present disclosure.

As illustrated in FIG. 3A, an embodiment of loading unit 200 includes a plurality of cam bars 131 for interacting with pushers 600 to deploy surgical fasteners 138. In the illustrated embodiment, pusher 600 includes three body portions 608, 610, 612, each of which being configured to engaging a single surgical fastener 138. Moreover, the apparatus disclosed in U.S. Pat. No. 5,318,221, the disclosure of which is hereby incorporated by reference herein, in its entirety, has a cam bar adapter that holds a plurality of cam bars and a knife. A channel is advanced through operation of the handle of the apparatus, which drives the cam bars and knife forward. A clamp tube that surrounds the proximal end of the anvil is advanced to clamp the anvil and cartridge together.

Figure 3B:
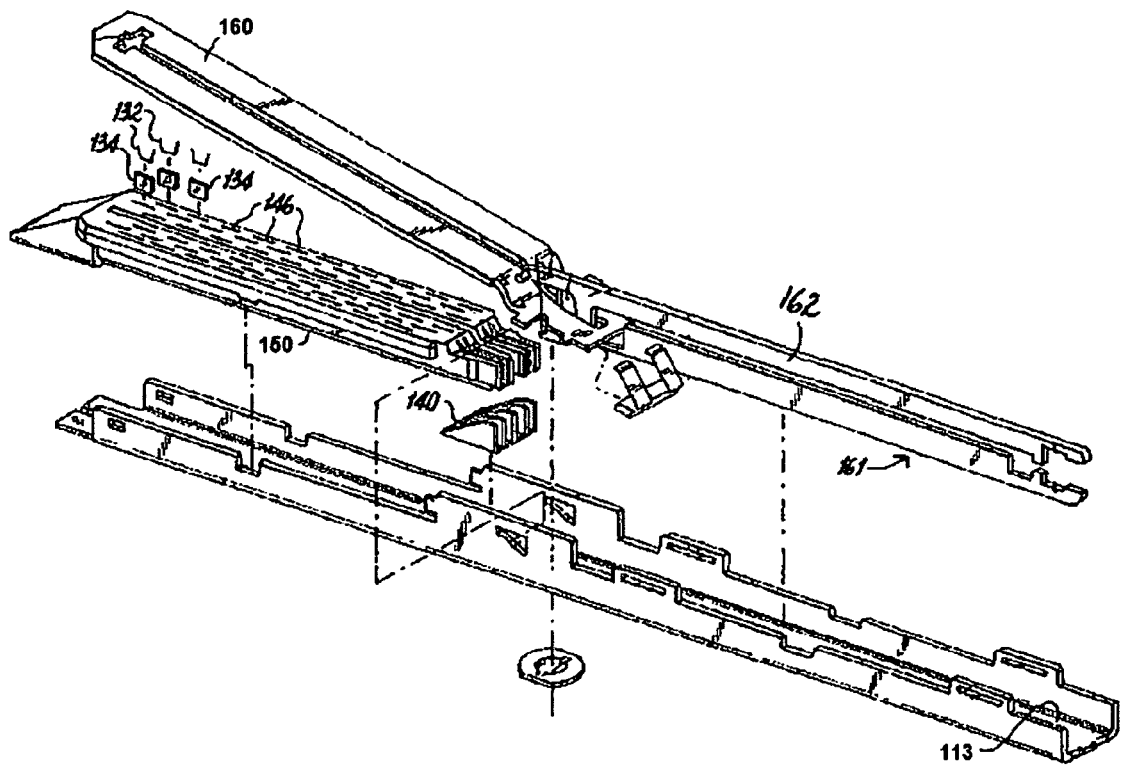
FIG. 3B is an exploded perspective view of a loading unit in accordance with an embodiment of the present disclosure.

As shown in FIG. 3B, an embodiment of loading unit 200 includes a drive assembly 161 having an elongated drive beam 162 that is advanced distally upon actuation of movable handle 112. The distal end of the drive beam 162 engages anvil assembly 160 and the channel 113 that supports cartridge assembly 150 as the drive beam 162 travels distally. Upon distal translation, the drive beam 162 engages pushers 134 which deploy the staples 132 from staple-retaining slots 146, and clamps anvil assembly 160 and cartridge assembly 150 together. The apparatus disclosed in U.S. Pat. No. 5,782,396, the disclosure of which is hereby incorporated by reference herein, in its entirety, discloses additional details of this embodiment.

Referring now to FIGS. 2 and 3, loading unit 200 is illustrated having flexible member attachment structures 300. Specifically, in this embodiment cartridge assembly 150 includes a first flexible member attachment structure $300_{CD}$ disposed on a distal portion of loading unit 200, and anvil assembly 160 includes a second flexible member attachment structure $300_{AD}$ disposed on a distal portion of loading unit 200. As shown, flexible member attachment structures 300 are disposed on an inner portion of the curve of jaw members 140. It is also envisioned that flexible member attachment structures 300 are disposed along an outer portion of the curve, or a combination of the inner and outer portions. With respect to linear jaw members 140, such as the jaw members 140 illustrated in FIG. 1A, it is envisioned that flexible member attachment structures 300 are disposed along either lateral side of jaw members 140. It is also envisioned that flexible member attachment structures 300 extend upwardly from the upper jaw member (e.g., anvil assembly 160) and/or downwardly from the lower jaw member (e.g., cartridge assembly 150). Additionally, while flexible member attachment structures $300_{CD}$ and $300_{CD}$ are shown as being substantially vertically aligned, it is envisioned that flexible member attachment structures 300 of the present disclosure are vertically out of alignment. As discussed herein, flexible member attachment structures 300 are configured to facilitate attaching a flexible member "S" (see FIGS. 4-6) to various portions of tool assembly 220 of loading unit 200. It is envisioned that flexible member "S" includes at least one of a suture, strap, cord, and the like.

Flexible member attachment structures 300 are shown in FIGS. 2 and 3 as hook-like members protruding from a lateral side of the respective jaw members 140. It is envisioned and within the scope of the present disclosure that flexible member attachment structures 300 are integrally formed with a particular jaw member 140, or otherwise extend therefrom.

Figure 4A:
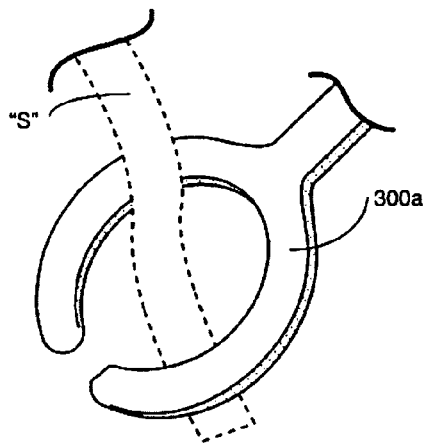
FIGS. 4A-4E illustrate various types of flexible member attachment structures in accordance with the present disclosure.
Figure 4B:
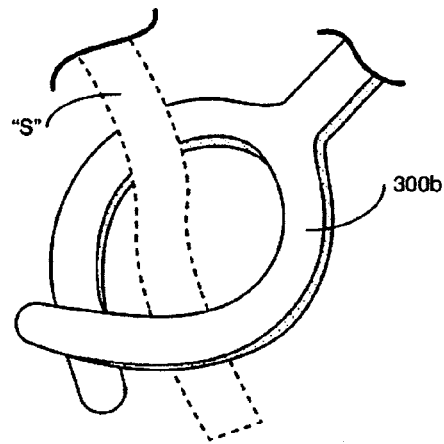
Figure 4C:
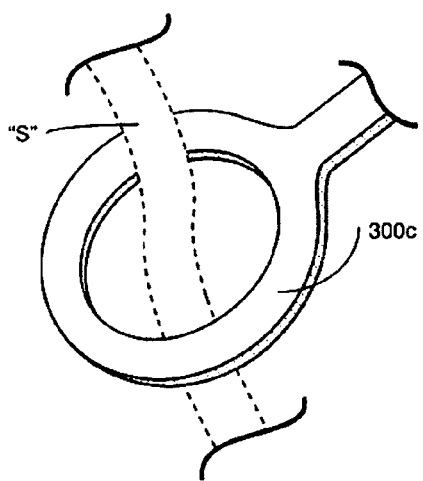
Figure 4D:
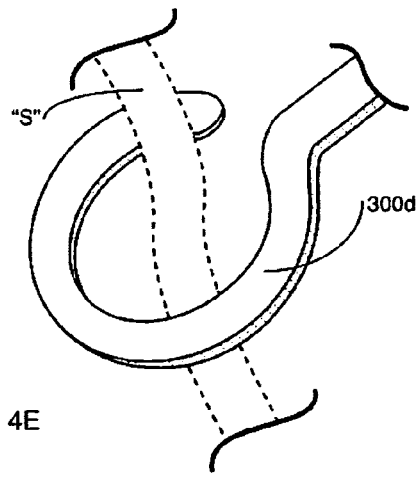
Figure 4E:
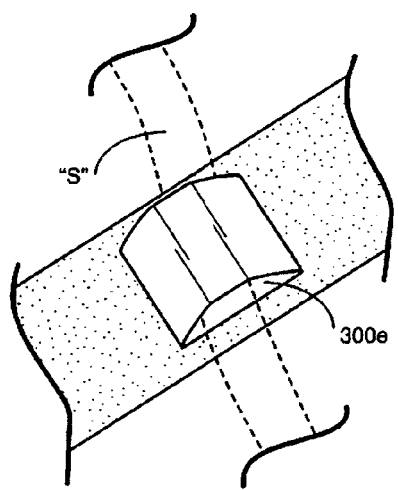

Examples of flexible member attachment structures 300 in accordance with the present disclosure are illustrated in FIGS. 4A-4D. In particular, flexible member attachment structure 300a in FIG. 4A includes two arms with an opening therebetween, such that a flexible member "S" can be squeezed therein and therefrom. In FIG. 4B, flexible member attachment structure 300b includes two flexible arms. In FIG. 4C, flexible member attachment structure 300c includes a closed loop. In FIG. 4D, flexible member attachment structure 300d includes a single arm and an opening. In FIG. 4E, flexible member attachment structure 300e is integrally formed with a jaw member 140 and includes a channel for threading a flexible member "S" therethrough. In each of the embodiments disclosed herein, flexible member attachment structures 300 may be removable from jaw members 140, or may be permanently attached thereto. As can be appreciated, many different other types of flexible member attachment structures are contemplated by the present disclosure.

Additionally, it is envisioned that flexible member "S" can be removably attached to jaw members 140 by a temporary attachment structure, such as glue, tape, etc. Further, at least one flexible member attachment structure 300 may include a strap having a connection feature (e.g., a hook and loop fastener commonly sold under the trademark VELCRO) to quickly capture tissue. In such an embodiment, the use of a flexible member "S" may not be needed.

Referring now to FIGS. 5A-5C, the utilization of flexible member attachment structures 300 is shown according to embodiments of the present disclosure. Flexible member attachment structures 300 are configured for use with a flexible member "S" to encircle target tissue (e.g., a patient's bowel) prior to sealing the tissue. After the tissue is encircled, a surgeon may perform a washout procedure, e.g., to effectively remove cells (e.g., malignant cells) from the tissue (e.g., bowel). A washout procedure is when a surgeon flushes the tissue that will be placed between the jaws of the surgical instrument 100 and fastened. The flexible member that is wrapped around the tissue may be used to control the flow of the fluid used in the washout procedure. A surgical procedure (e.g., a lower anterior resection) may then be performed after the washout procedure. Alternatively, if a physician chooses not to utilize flexible member attachment structures 300 and chooses not to perform a washout procedure, surgical instrument 100 (including flexible member attachment structures 300) may still be used to perform a suitable surgical procedure. That is, flexible member attachment structures 300 do not interfere with the typical use of a surgical instrument 100.

With continued reference to FIGS. 5A-5C, flexible member "S" is initially threaded through flexible member attachment structure $300_{AD}$ and then through flexible member attachment structure $300_{CD}$. A loop "L" is created adjacent a first free end "F1" of the flexible member "S." Additionally, the flexible member "S" may be wrapped around or tied to a flexible member attachment structure (e.g., $300_{AD}$). The distal end of jaw members 140 is then placed adjacent target tissue "T" (FIG. 5A). Jaw members 140 are then moved towards and into contact with the target tissue "T," which causes a second free end "F2" of the flexible member "S" to move relative to flexible member attachment structure $300_{CD}$. As a result, the flexible member "S" is pulled proximally within jaw members 140 (FIG. 5B). Next, the second free end "F2" of the flexible member is threaded through the loop "L" adjacent the first free end "F1" (FIG. 5C), thus encircling the target tissue "T." Finally, the second free end "F2" is pulled in the substantial direction of arrow "P" (FIG. 5C) to cinch down on and constrict the target tissue "T." After the target tissue "T" is constricted, the surgeon may perform a washout procedure.

Figure 6A:
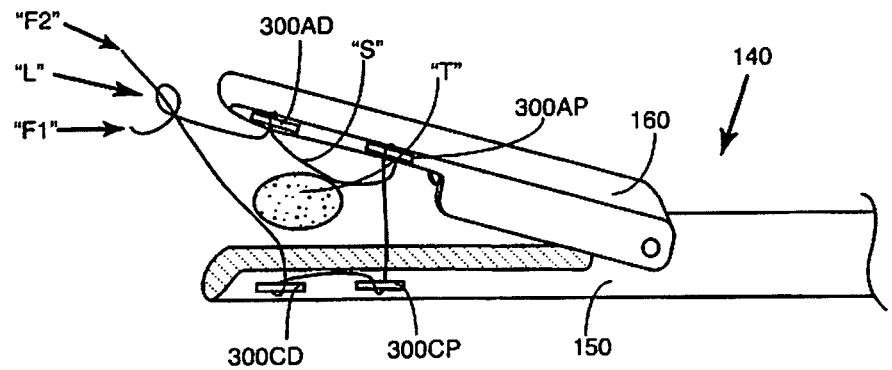
FIGS. 6A-6C are schematic side views of the jaw members showing flexible member attachment structures at various locations, and illustrating flexible member encircling target tissue.
Figure 6B:
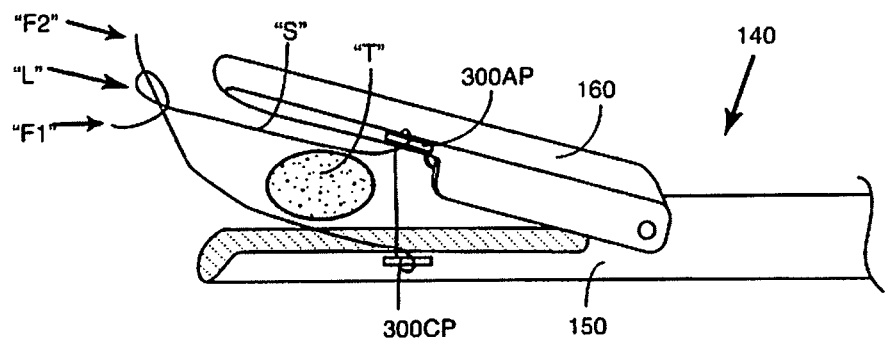
Figure 6C:
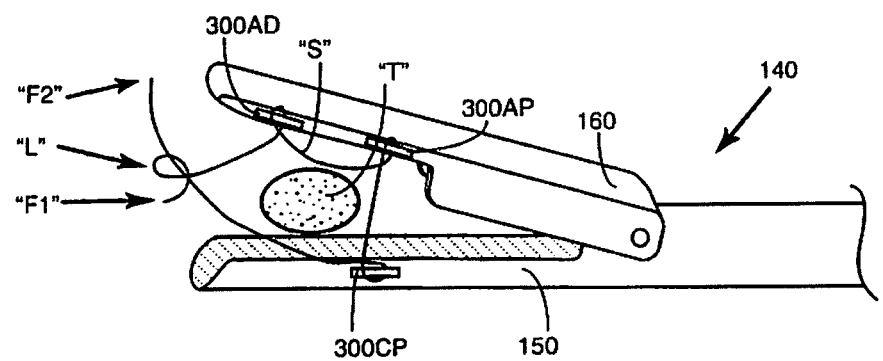

With reference to FIGS. 6A-6C, jaw members 140 are shown with various configurations of flexible member attachment structures 300, in accordance with embodiments of the present disclosure. In particular, the embodiment illustrated in FIG. 6A includes anvil assembly 160 having proximal and distal flexible member attachment structures $300_{AP}$ and $300_{AD}$, respectively, and cartridge assembly 150 having proximal and distal flexible member attachment structures $300_{CP}$ and $300_{CD}$, respectively. The embodiment illustrated in FIG. 6B includes anvil assembly 160 having a proximal flexible member attachment structure $300_{AP}$, and cartridge assembly 150 having a proximal flexible member attachment structure $300_{CP}$. The embodiment illustrated in FIG. 6C includes anvil assembly 160 having proximal and distal flexible member attachment structures $300_{AP}$ and $300_{AD}$, respectively, and cartridge assembly 150 having a proximal flexible member attachment structure $300_{CP}$. Each of FIGS. 6A-6C also illustrates flexible member "S" encircling target tissue "T," with the second free end "F2" disposed through the loop "L" adjacent the first free end "F1." As can be appreciated, the quantity and locations of flexible member attachment structures 300 are not limited by the illustrated embodiments, as one skilled in the art can envision any number of flexible member attachment structures 300 disposed anywhere on loading unit 200.

Additionally, while not explicitly illustrated in the accompanying figures, it is also envisioned that flexible member "S" is pre-tied onto jaw members 140 to allow the user to pull one end of flexible member "S" to capture tissue. For example, the flexible member can form a slip knot and a loop of the flexible member can extend around the jaw member of the instrument.

In another embodiment of the present disclosure, a separate instrument (not explicitly shown in the illustrated embodiments), either separate from surgical instrument 100, attachable to surgical instrument 100, or integrally formed with surgical instrument 100, can be used to thread flexible member "S" through flexible member attachment structure(s) 300, thread flexible member "S" through loop "L," rotate flexible member "S" around target tissue "T," and/or pull flexible member "S" to cinch down on and constrict target tissue "T." Such an instrument may be attachable to handle portion 110 of surgical instrument 100 and may include a separate actuation mechanism to longitudinally advance and/or rotate a distal portion of the instrument. It is envisioned that a grasper can be used to manipulate the flexible member. Additionally, a tissue clamp can be used to manipulate the flexible member or assist in clamping the tissue to facilitate the washout procedure. Suitable graspers and clamps are disclosed in U.S. patent application Ser. Nos. 12/414,918 and 12/467,324, the entire contents of each of which are incorporated by reference herein.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A surgical instrument for surgically joining tissue, the surgical instrument comprising:
   a handle portion;
   an endoscopic portion extending distally from the handle portion and defining a first longitudinal axis;
   a pair of jaw members disposed adjacent a distal end of the endoscopic portion and extending generally distally therefrom, at least one of the jaw members being movable with respect to the other between an open position and an approximated position for engaging body tissue therebetween, wherein both of the jaw members extend from the same endoscopic portion as each other; and
   a first flexible member attachment structure and a second flexible member attachment structure disposed in mechanical cooperation with a lateral side of each jaw member, the flexible member attachment structures being configured to facilitate the attachment of a flexible member thereto;
   wherein at least one flexible member attachment structure includes a hook protruding from a lateral side of its respective jaw member.

2. The surgical instrument of claim 1, wherein the jaw members are curved with respect to the first longitudinal axis.

3. The surgical instrument of claim 2, wherein each flexible member attachment structure is disposed along an inner portion of the curve of its respective jaw member.

4. The surgical instrument of claim 1, wherein each jaw member includes a proximal portion and a distal portion, the proximal portion being the longitudinal half of the jaw member that is closer to the handle portion, the distal portion being the longitudinal half of the jaw member that is farther away from the handle portion, and wherein the first flexible member attachment structure of each jaw member extends from the proximal portion and the second flexible member attachment structure of each jaw member extends from the distal portion.

5. The surgical instrument of claim 1, wherein the first and the second flexible member attachment structures disposed in mechanical cooperation with the first jaw member are substantially identical to the first and the second flexible member attachment structures disposed in mechanical cooperation with the second jaw member.

6. The surgical instrument of claim 1, wherein one of the jaw members includes a tissue-contacting surface defining a plane, and wherein the entirety of each flexible member attachment structure is spaced from the plane when the jaw members are in the approximated position.

7. The surgical instrument of claim 1, wherein each of the jaw members includes a length and a tissue contacting surface extending along a majority of the entire length, and wherein the tissue contacting surfaces of both of the jaw members are substantially parallel to each other when the jaw members are in the approximated position.

8. The surgical instrument of claim 1, wherein the jaw members are linearly disposed with respect to the first longitudinal axis.

9. The surgical instrument of claim 1, wherein at least one jaw member is pivotable with respect to the endoscopic portion.

* * * * *